United States Patent [19]

Heiss et al.

[11] 4,025,543
[45] May 24, 1977

[54] PROCESS FOR THE PREPARATION OF 1,4-NAPHTHODINITRILE

[75] Inventors: Lorenz Heiss, Hofheim, Taunus; Klaus Uhl, Neuenhain, Taunus, both of Germany

[73] Assignee: Hoechst Aktiengesellschaft, Frankfurt am Main, Germany

[22] Filed: Jan. 23, 1976

[21] Appl. No.: 651,699

[30] Foreign Application Priority Data

Jan. 28, 1975  Germany .......................... 2503321

[52] U.S. Cl. .......................................... 260/465 H
[51] Int. Cl.$^2$ ...................................... C07C 121/62
[58] Field of Search ................................ 260/465 H

[56] References Cited

UNITED STATES PATENTS 3,501,470  3/1970  Grasselli et al. ........... 260/465 H X

*Primary Examiner*—Dolph H. Torrence
*Attorney, Agent, or Firm*—Connolly and Hutz

[57] ABSTRACT

Process for the preparation of 1,4-naphthodinitrile, by reacting o-phenylene-diacetonitrile with a glyoxalbisaldimine. By this process the 1,4-naphthodinitrile is easily obtained in a one-step process. This compound is an important intermediate for the production of 1,4-naphthalene-dicarboxylic acid.

3 Claims, No Drawings

PROCESS FOR THE PREPARATION OF 1,4-NAPHTHODINITRILE

The present invention provides a process for the preparation of 1,4-naphtodinitrile, which comprises reacting o-phenylene-diaceto-nitrile with a glyoxal-bisaldimine.

These glyoxalbisaldimines have the general formula $$R - N = CH - CH = N - R,$$

wherein R represents an alkyl, a cycloalkyl, or an optionally substituted aryl group. They are prepared, according to I. M. Kliegmann and R. K. Barnes (Tetrahedron 26, 2555 and J. Org. Chem. 35 (1970) 3140), by a reaction of glyoxal and a corresponding amine in water or alcohol at room temperature, and by suction-filtration or separation — possibly at a lower temperature — of the crystallized or separated aldimine. As primary aliphatic amines for the preparation of the aldimines there may be mentioned, for example, propylamine, isopropylamine, n-butylamine, secondary butylamine, tertiary butylamine, cyclohexylamine; as aromatic amines there may be used, for example, 1-amino-2-methylbenzene, 1-amino-2,4,6-tri-methylbenzene, 1-amino-4-methyl-benzene, 1-amino-4-chlorobenzene, 1-amino-4-nitrobenzene, 1-amino-2,6-dimethybenzene, 1-amino-2,4-dimethylbenzene, or 1-amino-2,5-dimethylbenzene.

According to the directions given by Thorpe (J. Chem. Soc. 93 (1908), 175), o-phenylene-diacetonitrile can be prepared in a good yield by using o-xylylene-halide and potassium cyanide and/or sodium cyanide, in accordance with the following formula scheme:

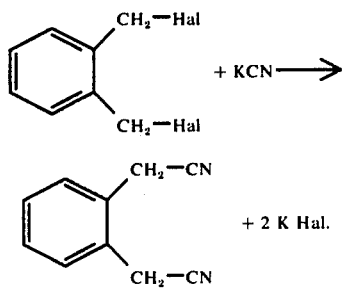

The cyclization of the o-phenylene-diacetonitrile with the glyoxalbisaldimine to yield the 1,4-naphthodinitrile may be achieved by simply heating the components at a temperature of from 30° to 160° C, the yield and the purity of the reaction product being increased by an aprotic solvent, such as dimethylformamide or dimethylsulfoxide. The use of lower aliphatic aldimines has the advantage that the amine obtained in the process of cyclization is immediately eliminated by distillation and can be used again. The addition of basic catalysts results in a better yield, especially in the case of aromatic aldimines. Slightly basic catalysts are advantageous, such as sodium acetate, potassium carbonate or sodium hydroxide solution, preferably in an amount of from 0.1 to 10 molar percent. Owing to its being difficulty soluble, the 1,4-naphthodinitrile formed may be suction-filtered directly from the solvent and is obtained in its pure form without any further recrystallization.

It was a surprising fact which could not have been foreseen that 1,4-naphthodinitrile could be obtained in this manner, as the reaction of o-phenylene-diacetonitrile with glyoxal itself or the derivatives thereof, for example, glyoxalbisulfite, glyoxalacetate, glyoxalchloracetate, glyoxalacylal, tetraaminoethane or 1,2-dialkoxy-1,2-diaminoethane, in various reaction media does not yield 1,4-naphthodinitrile.

The process of the invention uses starting products which are easily accessible and yields the desired final product in a single-step process, whereas, on the other hand, it has not been possible so far to obtain 1,4-naphthodinitrile but by means of a complicated multi-stage process (Lindstead et al. J. Chem. Soc. 1936, 1942).

1,4-Naphthodinitrile is an important intermediate product for organic chemistry. Thus, for example, iminoethers and amidines are obtained by reacting 1,4-naphthodinitrile with alcohols and amines. By saponifying 1,4-naphthodinitrile with alkalis and acids, 1,4-naphthaline-dicarboxylic acids are obtained which are important starting compounds for the preparation of optical brighteners.

The following Examples serve to illustrate the invention.

EXAMPLE 1

15.6 g (0.1 mole) of o-phenylene-diacetonitrile were heated at 115° C, and 26.4 g (0.12 mole) of N-cyclohexylamineglyoxalbisaldimine were introduced portionwise within 40 minutes. The reaction was completed at a temperature of from 120 to 125° C, while stirring, subsequently the reaction mixture was cooled, was boiled with 30 ml of methanol, and the reaction product was suction-filtered, after the mixture had been cooled again to 10° C. Finally the product was washed with cold methanol. 6.5 Grams of 1,4-naphtodinitrile were obtained which had a melting point of 209° C (Literature: Lindstead, J. Chem. Soc. 1936, 1739, melting point 208° C).

EXAMPLE 2

15.6 Grams (0.1 mole) of o-phenylene-diacetonitrile, 20.1 g (0.1 mole) of N-(tertiary)-butylamine-glyoxalbisaldimine and 50 ml of dimethyl-formamide were heated at 130° C for 1 hour, while stirring, and the stirring was continued for 3 to 4 hours at a temperature of from 130° to 135° C. In the course of this process 16 ml of tertiary butylamine (corresponding to 83.5% of reacted aldimine) were distilled off. After the reaction mixture had been cooled to 10° to 20° C, the crystal paste formed was suction-filtered, was washed with cold methanol and dried. Yield: 12 g of 1,4-naphthodinitrile (68.5% of the theory). Melting point: 209° C.

EXAMPLE 3

15.6 Grams (0.1 mole) of o-phenylene-diacetonitrile, 26 g (0.11 mole) of N-o-toluidine-glyoxalbisaldimine and 50 ml of dimethylsulfoxide were dissolved by heating at 50° C, subsequently 1 g of pulverized potassium hydroxide solution was added, and the reaction mixture was heated further at a temperature of from 90 to 95° C. After the mixture had been stirred again for 3 to 4 hours at 95° C, it was cooled to 10° C, and the crystal paste was suction-filtered and washed with cold methanol. 11.2 Grams of 1,4-naphthodinitrile were obtained, which corresponded to a yield of 63% of the theory. The melting point was 208° C.

We claim:

1. Process for the preparation of 1,4-naphthodinitrile, which comprises heating at a temperature of from 30° to 160° C o-phenylene-diacetonitrile with a compound of the formula

wherein R is alkyl with 1 to 4 carbon atoms, cyclohexyl or phenyl which is substituted by 1 to 3 of the substitutents chlorine, methyl or nitro.

2. Process as claimed in claim 1, which comprises carrying out the reaction in the presence of an aprotic solvent.

3. Process as claimed in claim 1, which comprises carrying out the reaction in the presence of a basic catalyst.